US006719711B1

(12) United States Patent
Islava

(10) Patent No.: US 6,719,711 B1
(45) Date of Patent: Apr. 13, 2004

(54) INFLATABLE SPLINT AND METHOD OF USING THE SAME

(75) Inventor: Steve Islava, Newport Beach, CA (US)

(73) Assignee: STI Medical, Newport Beach, CA (US)

( * ) Notice: Subject to any disclaimer, the term of this patent is extended or adjusted under 35 U.S.C. 154(b) by 0 days.

(21) Appl. No.: 09/569,694

(22) Filed: May 11, 2000

(51) Int. Cl.⁷ .................................................. A61F 5/00
(52) U.S. Cl. ..................... 602/13; 602/20; 128/DIG. 20
(58) Field of Search ............................... 602/5, 13, 18, 602/19, 20, 21; 128/846, 877, 878, 879, DIG. 20

(56) References Cited

U.S. PATENT DOCUMENTS

| 3,048,860 A | * | 8/1962 | Richardson | 128/DIG. 23 |
| 3,164,152 A | * | 1/1965 | Nicoll | 602/13 |
| 3,701,349 A | * | 10/1972 | Larson | 602/13 |
| 4,964,402 A | * | 10/1990 | Grim | 128/804 |
| 6,007,395 A | * | 12/1999 | Kroll | 441/106 |
| 6,071,257 A | * | 6/2000 | Stojanovic | 602/18 |

* cited by examiner

Primary Examiner—Michael A. Brown

(57) ABSTRACT

An inflatable splint comprises a plurality of air chambers divided by latitudinal and longitudinal divisions. The latitudinal division comprises perforated latitudinal welds which divide the splint into portions, or rows of air chambers. Each portion is detachable or separable from an adjacent portion and adapted to wrap around a section of a body part independently of the other portion. The splint is bendable at the latitudinal divisions to accommodate joints and various bends in an injured limb. Each portion is capable of forming a U-structure to retain a section of an injured limb. The latitudinal divisions enable each portion to bend away from each other or toward each other, in which case one U-structure may be disposed at least in part within another U-structure. Adjustable fasteners are provided for each portion. A method for securing an injured limb is also provided.

28 Claims, 5 Drawing Sheets

INFLATABLE SPLINT AND METHOD OF USING THE SAME

BACKGROUND OF THE INVENTION

1. Field of the Invention

The invention relates generally to inflatable splints.

2. Description of Related Art

Many problems exist with the prior art which includes cardboard splints and inflatable splints. Cardboard splints are bulky and thus, incapable of being disposed in a trauma box. When applied to an injured area, cardboard splints leave large voids which must be filled with dressings and other material, thus leading to a greater expense. In order to treat a joint or an angled fracture, cardboard splints must be manually cut and taped.

Current inflatable splints consist of sleeves having a single air container that is entirely inflated. After sliding the sleeve onto a target area, the splint is automatically inflated to its maximum extent. Thus, current inflatable splints tend to restrict blood flow to a wounded area, which can be highly detrimental for recovery. Since current inflatable splints also do not allow for any structural adjustment once they are inflated, such splints do not accommodate body parts having bends. This poses a problem for securing joints, broken bones, and any other body part having bends, such as the wrist, elbow knee or foot.

The prior art splints also do not allow for a physician to conveniently examine an injured area or a portion thereof. With cardboard splints, physicians must completely cut the tape securing the splint, remove any dressings, and then re-tape the splint after examination in order to secure the injured area. Inflatable splints must be completely removed in order for a physician to examine any area covered within.

BRIEF SUMMARY OF THE INVENTION

An inflatable splint comprises a plurality of interconnected or communicated air chambers divided by welds. A plurality of longitudinal welds divide the splint into a plurality of cylindrical interconnected air chambers, each of which generally has a longitudinal axis aligned with the direction of the limb or a portion of the limb around which that portion of the splint is wrapped. The interconnected air chambers are also divided by perforated latitudinal welds which preferably are defined perpendicular to the longitudinal welds, thereby defining each air chamber into at least two portions. Each portion is detachable from the adjacent portion by tearing on the perforation defined through the latitudinal welds defining the two portions. Each portion is thus adapted to being wrapped around a limb, portion of a limb or other body part independently from the other portion. The splint is bendable at the latitudinal dividing lines to accommodate joints and various bends of a limb or portion of a limb. Each portion is capable of being formed into an open U-structure curved in a plane generally parallel to the latitudinal welds to stabilize a bent limb or portion thereof. The latitudinal dividing lines enable each open U-shaped portion to bend away from or toward another adjacent open U-shaped portion, in which case one U-structure may be disposed or nested at least in part within another adjacent U-structure. Adjustable fasteners are provided for each portion to bind the open upper edges of the U-structure together or at least in a fixed relationship to each other. A method for securing an injured limb with such a splint is also provided.

More specifically, the invention is defined as an inflatable splint comprising a first portion including a first plurality of air chambers and a first plurality of longitudinal divisions separating the first plurality of air chambers. A second portion includes a second plurality of air chambers and a second plurality of longitudinal divisions separating the second plurality of air chambers. At least one separable latitudinal division is disposed between the first portion and the second portion.

The separable latitudinal division comprises at least one latitudinal weld with a perforation defined at least on part of the weld. The perforated latitudinal division enables the first portion to fold toward or away from the second portion. The second portion is detachable at least in part from the first portion by way of the perforated latitudinal division. The first portion is adapted to wrap around a first extremity of a human body. The first and second portions are each capable of forming a first U-structure. The second U-structure is capable of being disposed at least in part within the first U-structure.

The splint further comprises a blow spout coupled to at least one air chamber and wherein the air chambers are intercommunicated with each other for form a common inflatable containment. The first portion further comprises a first fastener to couple a first edge of the first portion to a second edge of the first portion. The second portion further comprises a second fastener to couple a right edge of the second portion to a left edge of the second portion. The first fastener and the second fastener each comprise a Velcro strap.

The first portion further comprises a strip to couple the first portion to second first portion when the first and second portions are disposed adjacent to each other. The strip comprises double sticky tape adhered to the first portion and capable when a release strip is removed to adhere to the second portion when the first and second portions are disposed adjacent to each other.

Alternatively stated, the inflatable splint comprises a plurality of longitudinal air chambers disposed side by side, and a plurality of longitudinal welds separating the air chambers disposed side by side. The splint further comprises at least one latitudinal weld disposed between at least two adjacent longitudinal air chambers. The latitudinal weld is perforated.

The invention is also characterized as a method for securing an extremity of a human body, the method comprising the steps of providing an inflatable splint with a first portion and a second portion, segmenting the first portion and the second portion with longitudinal welds to provide longitudinal air chambers, and separating the first portion from the second portion with at least one latitudinal weld.

The method further comprises the step of perforating the latitudinal weld or detaching at least in part the first portion from the second portion. The splint is inflated and the first portion wrapped around the extremity. In wrapping the first portion around the extremity a first U-structure is formed with the first portion. The method further comprises the step of fastening a left side of the first portion to a right side of the first portion. The second portion is wrapped around a body part adjacent to the extremity in which a second U-structure is formed with the second portion. A left side of the second portion is fastened to a right side of the second portion. The first portion may be bent toward or away from the second portion.

The invention, now having been briefly summarized, may be better visualized by turning to the following drawings wherein like elements are referenced by like numerals.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS

Figure 1A:
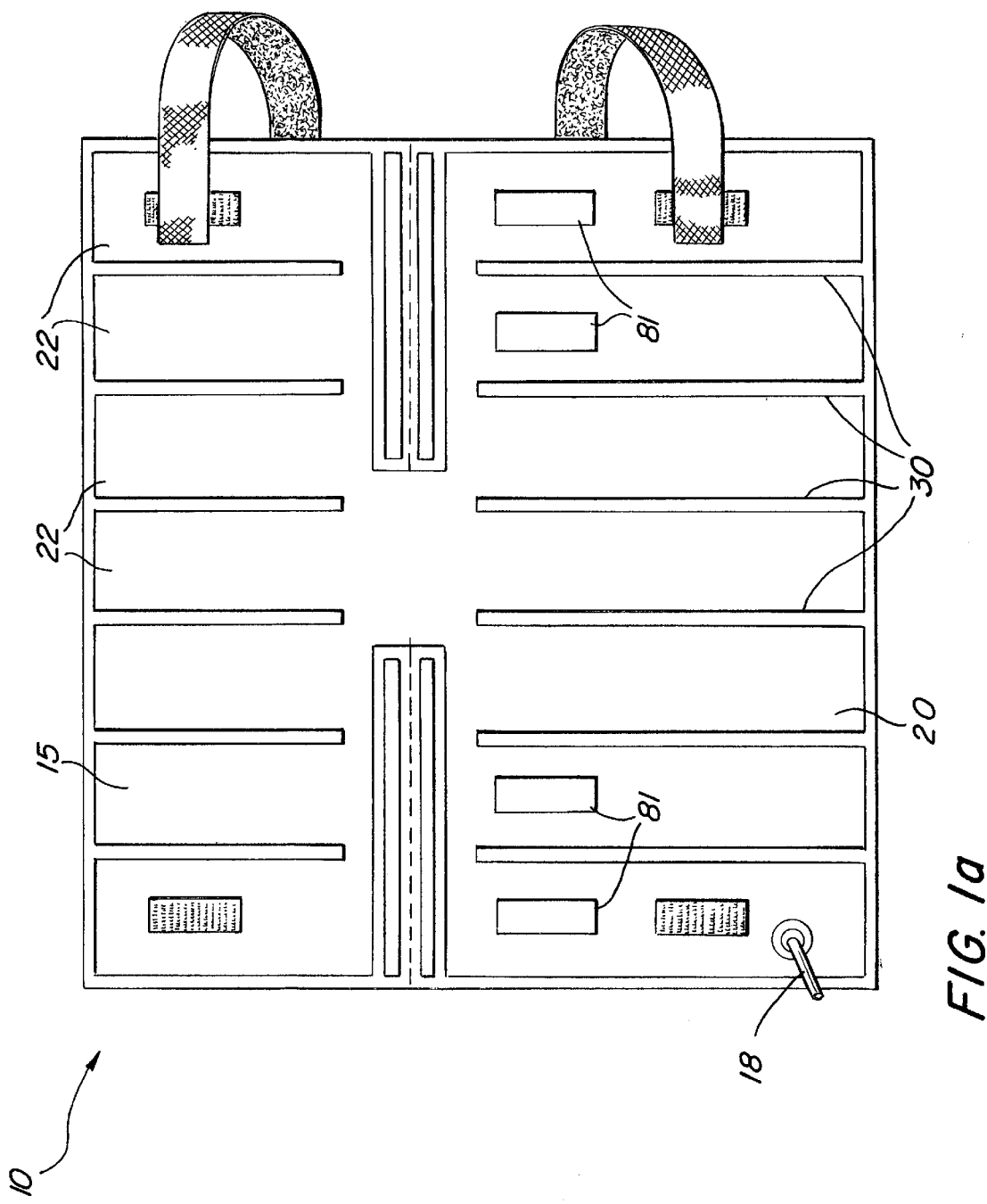
FIG. 1a is a plan view of an inflatable splint shown as deflated.

In FIG. 1a, an inflatable splint 10 is adapted to hold various injured body parts or portions of the same, such as limbs, legs, knees, ankles, arms, wrists, necks and more. FIG. 1a illustrates the inflatable splint 10 in a deflated configuration. The splint 10 comprises a thin, flexible translucent material 15, such as nylon, vinyl, as well as other material suitable for an inflatable device. In the preferred embodiment polyofin is used for among other reasons its affinity to pressure adhesive described below. When deflated and not in use, the splint 10 occupies minimal space. Thus, the splint 10 may be made into a small package and very compactly stored, for instance, in a trauma box or a first aid kit. The splint 10 comprises a conventional blow spout 18 to enable a user to manually inflate the splint 10. An automatic inflating device may also be provided if desired. The splint 10 comprises an air container 20 which when inflated, as described below, forms multiple interconnected longitudinal air chambers 22 as defined by a plurality of longitudinal welds 30.

Figure 1B:
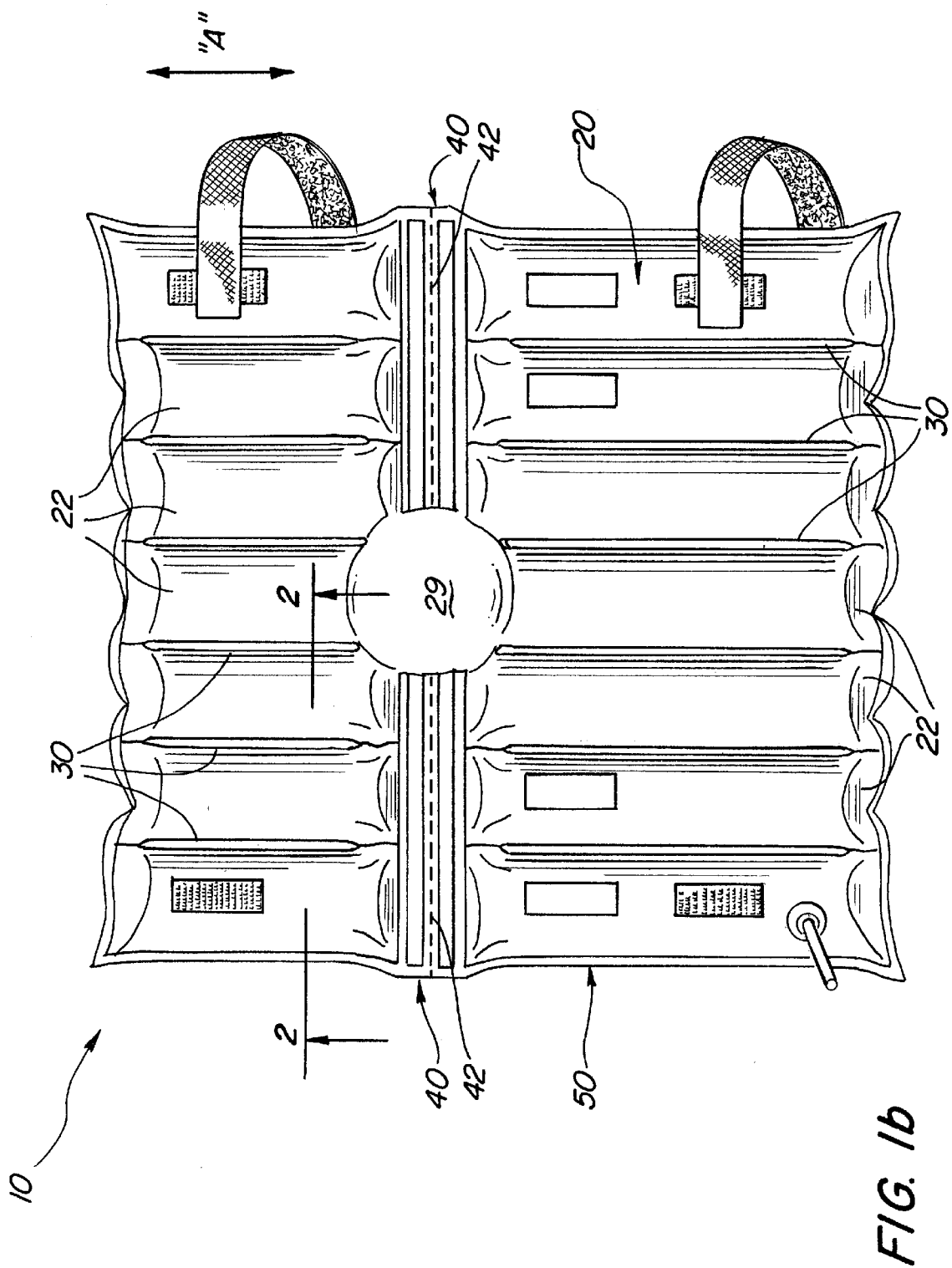
FIG. 1b is a plan view of the splint of FIG. 1a shown as inflated.

FIG. 1b is a plan view of the splint 10 as inflated. The inflatable splint 10 comprises a plurality of longitudinal air chambers 22 extending in a longitudinal direction denoted by reference symbol, "A". The interconnected multiple air chambers 22 are parts of the single air container 20 and, thus, are in pneumatic communication with each other. The single air container 20 is segmented by both longitudinal welds 30 such that the chambers 22 are disposed side-by-side and latitudinal welds 40 such that the chambers 22 are divided into two aligned portions disposed end-to-end. Welds 30 or 40 may be replaced by equivalent structural divisions such as seams, moldings and the like. The pair of latitudinal welds 40 extend from the sides of the splint 10 toward the center to divide the splint into multiple portions 50, 60 wherein each portion comprises rows of air chambers 22 disposed side-by-side. In the preferred embodiment, the latitudinal welds 40 do not extend across the entire width of the splint 10. Therefore, a center portion 29 of the splint 10 is not welded such that the air chamber 22 or chambers 22 in the center of the splint 10 extend from one end to the other without being divided latitudinally.

Figure 2:
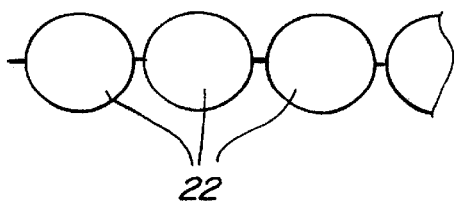
FIG. 2 is a cross-sectional view taken along lines 2—2 of FIG. 1b.

As shown in the cross-sectional view of FIG. 2, the air chambers 22 are cylindrical in profile when inflated. The latitudinal welds 40 are perforated, serrated or otherwise separable on a predetermined line. The serrated lines 42 are preferably torn by hand the paramedic in the field at the time of use of splint 10.

An advantageous feature of this invention is that the serrated latitudinal lines 42 allow the splint 10 to bend at the latitudinal welds 40 leaving the center portion 29 to serve as a hinge. In FIGS. 1a and 1b, a single serrated line 42 is shown to extend substantially across each latitudinal weld 40. However, it is to be expressly understood that the latitudinal dividing line 40 may comprise multiple serrated lines spaced apart from one another as well as non-serrated portions. If a single latitudinal weld 40 were provided to extend across the entire width of the splint, the perforation may also extend through the entire width of the splint 10. It is to be expressly understood that the splint 10 may comprise any number of air chambers 22 per row, and two or more rows.

Figure 3:
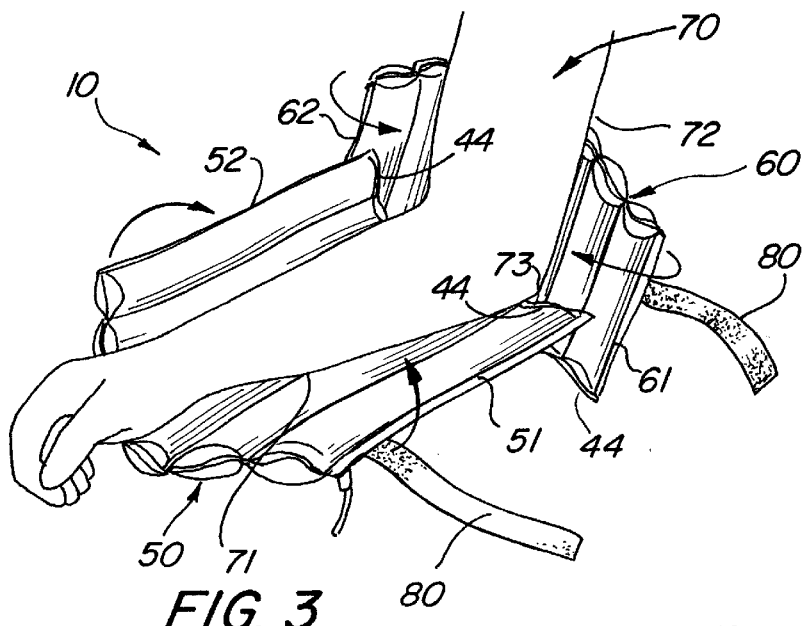
FIG. 3 is a perspective view of the splint in an intermediate position as it is first being applied to a bent arm.

FIG. 3 is a perspective view of the splint 10 in an intermediate configuration as it is being applied to a bent arm. To encompass a joint such as a knee or an elbow 73, the joint 73 is placed at or adjacent to the latitudinal weld 40. The serrated lines 42, shown in FIG. 1, allow the splint 10 to bend at the latitudinal weld 40. As shown in FIG. 3, each portion 50, 60 is folded and wrapped around the limb portions 71, 72, respectively, with the outer chambers 22 brought toward each other to wrap around a body part, such as the arm 70. In another aspect, a first edge 51 and an opposite second edge 52 are brought toward each other as they wrap around an extremity 71. Similarly, a first side 61 and a second side 62 of the second row 60 are brought toward each other as they wrap around a second body part 72 that is adjacent to the extremity 71. Thus, the first portion 50 and the second portion 60 each form an open U-structure as a result of the sides 51, 52, 61, 62 of each portion 50, 60, respectively, being brought toward each other. As discussed below a plurality of adhesive or Velcro straps 80 are provided to assist in this wrapping operation and to hold splint 10 into its wrapped configuration.

As shown in FIGS. 1a, 1b and 3, the first portion 50 may be detached at least in part from the second portion 60 by tearing along the serrated line 42, as indicated by detached ends 44 depicted in FIG. 3. This enables the first portion 50 to bend toward or away from the second portion 60. Detaching one portion 50 from another portion 60 also enables each portion to form a structure independently from the other. By detaching the portions 50, 60 along the perforated weld 40, the second portion 60 may be folded into a U-structure first while the first portion 50 remains unfolded, or vice versa. The unwelded center portion 29, as shown in FIG. 1a, serves as the flexure upon which the two portions 50, 60 bend toward or away from each other.

Each portion 50, 60 may be folded in a configuration that is different from a configuration of the other portion. In FIG. 3, for instance, the second portion 60 may be folded to a lesser degree in order to accommodate a larger body part, shown as the upper part 72 of the arm 70. The first portion 50 may be folded to a greater degree to wrap around a smaller body part, namely the forearm 71. Thus, each portion 50, 60 becomes its own customizable section wherein the sides 51, 52, 61, 62 of each portion 50, 60, respectively, may be folded more or less snugly to stabilize a section of the injured limb held therein.

Figure 4:
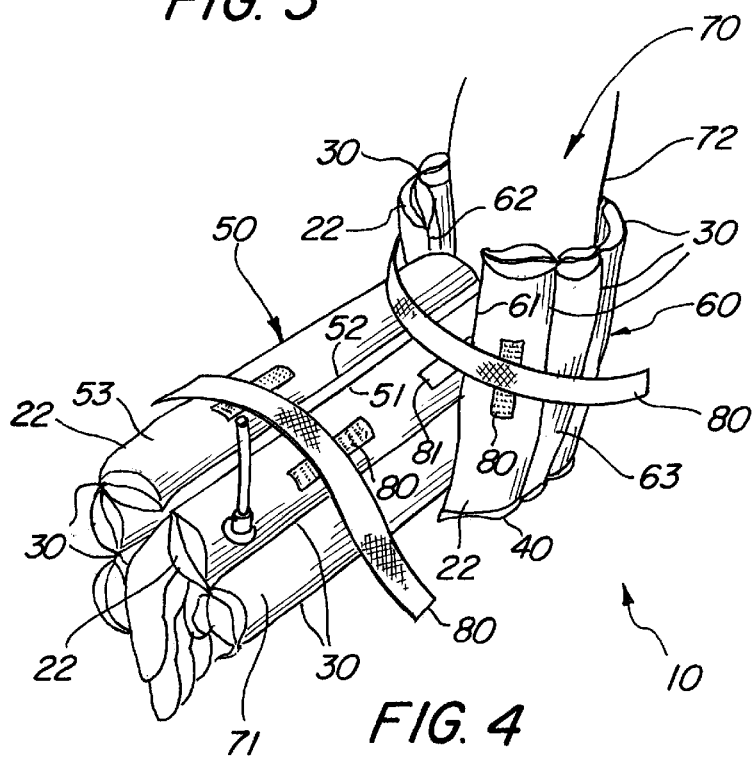
FIG. 4 is a perspective view of the splint of FIG. 3 in a curved, operative configuration after its installation on the arm of FIG. 3 has been completed.

FIG. 4 is a perspective view of the splint 10 in a completed operative configuration. The longitudinal welds 30 thus allow the air chambers of each portion 50, 60 to comfortably wrap around sections 71, 72 of limb 70 without restricting blood flow in any portion of it. The perforated latitudinal weld 40 allows one portion 50 to be partially detached from another portion 60 so as to enable the portions 50, 60 to bend toward or away from each other while independently maintaining their respective U-structures. As shown in FIG. 4, the result is that the U-structure of the first portion 50 may be disposed at least in part within the U-structure of the second portion 60. This provides an accommodating fit for an enveloping joint in splint 10 for an elbow or knee or for that matter any other bent portion of a fractured limb. The angle of the enveloping joint may be less than 90 degrees or nearly flat at almost 180 degrees.

Strap fasteners 80 are disposed on an external surface 53, 63 of each portion 50, 60, respectively. In the preferred embodiment, the fasteners 80 comprise two-part Velcro straps. One part of strap 80 is adhered to one edge of splint 10 and the opposing mating part of strap 80 is adhered to the opposing edge of splint 10. Various other fasteners can be used such as tape, a belt and buckle, ties and the like. The fasteners 80 couple an outer air chamber 22 adjacent to one side 51, 61 of a portion 50, 60, respectively, to an outer air chamber 22 adjacent to an opposite side 52, 62 of the same portion 50, 60, respectively. The fasteners 80 on each portion 50, 60 are adjustable, thereby allowing each portion 50, 60 to custom wrap a certain-sized section of the limb independently of the other portion. Furthermore, one portion 50 or 60 may be fastened while another portion left open and unfastened. This allows a patient or physician to examine, clean or access a portion of the injured body part without having to unfasten the entire splint 10.

In addition to the straps 80 a double sticky, or double-sided, adhesive strip 81 is disposed on the outside surface of either portion 50 or 60 or both as shown in FIG. 1a adjacent to the latitudinal welds 40. The strip 81 is adhered on one its sides to the chamber 22 and is provided with a conventional nonadhering release strip covering the adhesive bearing opposing side. When it is desired to use the strips 81, the release strip is removed and the adhesive bearing opposing side is pressed into contact with the opposing surface of the adjacent portion 50 or 60 after the desired bend has been established along weld 40. The preferred material used to form the air chamber 22 has a high affinity to conventional pressure adhesives and a secure fixation of portions 50 and 60 is thereby realized by means of strips 81.

Figure 5A:
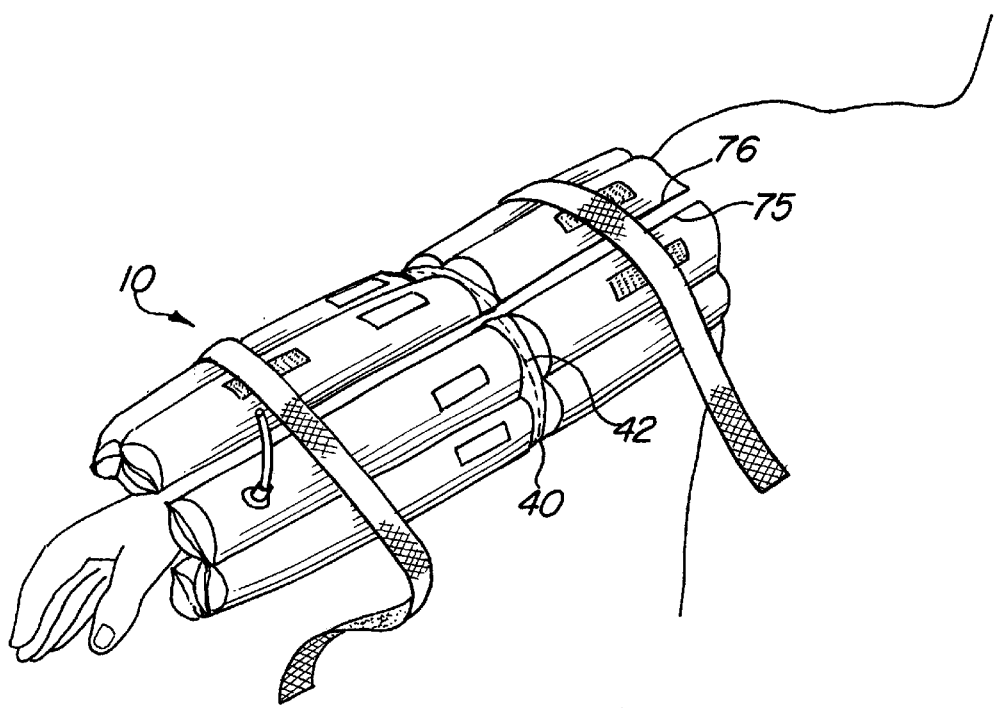
FIG. 5a is a perspective view of the splint in a straight operative configuration.

FIG. 5a shows the splint 10 in an alternative, operative configuration. If it is desired to keep the target area straight, the entire splint 10 may be wrapped around the target area 70 by folding one side 75 of the splint 10 toward the other side 76. The fasteners 80 couple the two sides 75, 76 together. Thus, the serrated lines 42 at the latitudinal welds 40 need not be torn, thus keeping the first portion 50 integral with the second portion 60.

Figure 5B:
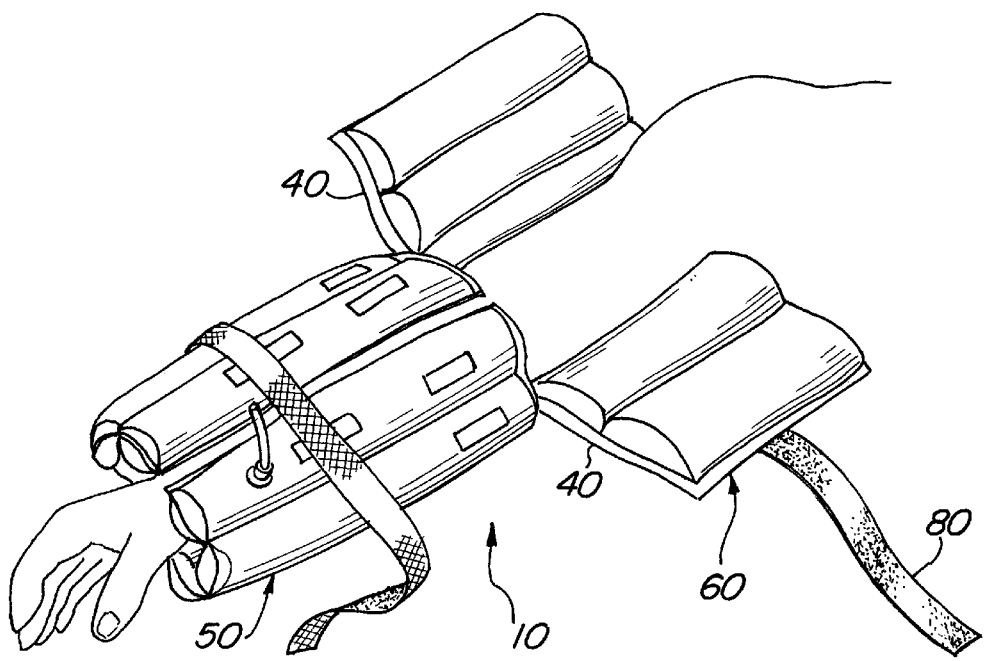
FIG. 5b is a perspective view of the splint illustrating a portion opened to provide access to a part of an injured area while the remainder of the splint remains secured.

FIG. 5b illustrates a major advantage of the splint 10 wherein one portion 60 may be unfastened and unfolded while the other portion 50 remains folded. The splint 10 enables a physician to examine a portion of an injured area without having to unwrap or undo the entire apparatus. To gain access to a portion of an injured area, the fastener 80 of the second portion 60 is unfastened. By tearing along the serrated lines 42 of the latitudinal welds 40 as shown in FIG. 5a, the second portion 60 may be opened up thereby enabling access to a part of the injured area while the remainder of the injured area remains secured. The splint 10 offers this capability regardless of whether it is in a straight or bent configuration. Furthermore, to rewrap the part of the injured area, the second portion 60 of the splint 10 simply needs to be folded and refastened with the fasteners 80. Thus, the splint 10 allows a user to open and close each portion thereof in order to examine a particular part of an injured area without having to unwrap and resecure the entire apparatus. Unlike the devices in the prior art, the serrated lines 42 at the latitudinal welds 40 provide this unique feature. Since the splint 10 comprises a translucent material, X-rays of a secured area may be taken without having to unwrap the splint 10.

Figure 6:
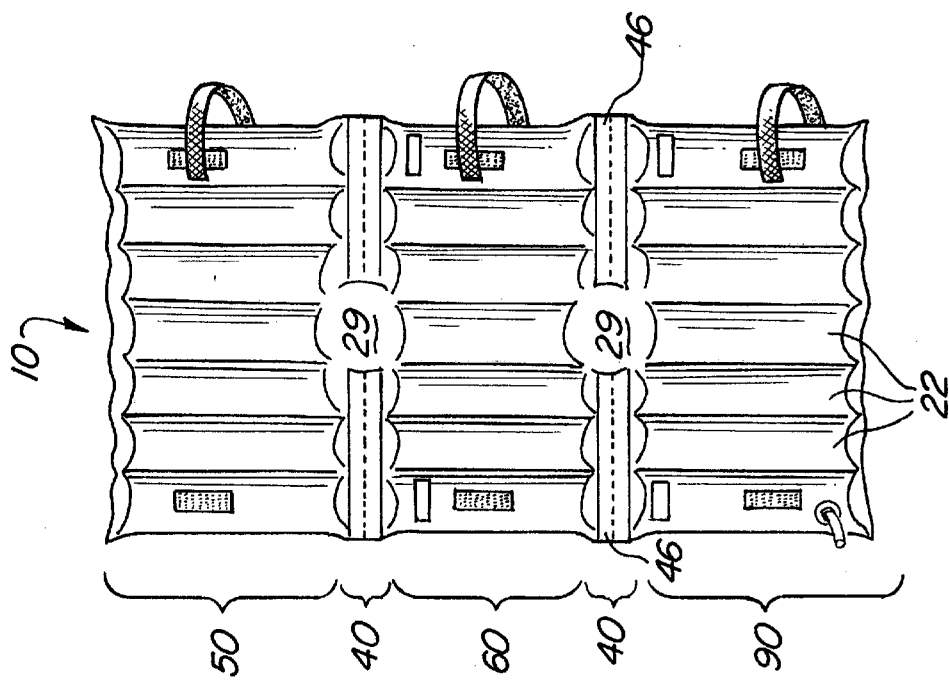
FIG. 6 is a plan view of an alternate embodiment of the splint.

FIG. 6 is a plan view of an alternate embodiment of the splint 10 wherein additional latitudinal rows are provided. In FIG. 6, an additional row 90 of air chambers 22 is provided and separated from an adjacent row 60 by additional latitudinal welds 46. Each latitudinal dividing line 40 comprises multiple latitudinal welds 46, including outer latitudinal welds 46 that are perforated. This enables a user to partially detach each row from another without being able to inadvertently remove an entire row. Thus, the non-welded center sections 29 serves to couple the rows 50, 60, 90 together and thus keep the splint 10 as one integral piece.

Figure 7:
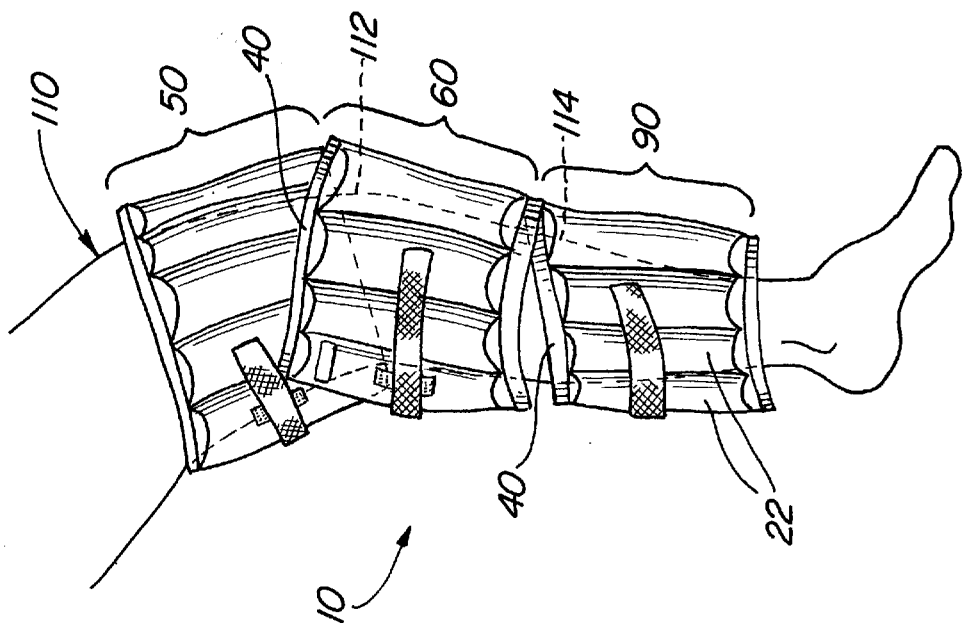
FIG. 7 is a perspective view of the alternate embodiment of FIG. 5 in an operative configuration.

FIG. 7 is a perspective view of the alternate embodiment of FIG. 6 in a fully installed configuration. It will be appreciated that providing an additional row 90 of air chambers 22 allows the splint 10 to stabilize a body part having multiple bends, such as a leg 110 with a knee 112 and a compound fracture 114. In FIG. 7, the splint 10 is applied with a middle row 60 bent away from the first row 50 at one perforated latitudinal weld 40 disposed adjacent to the knee 112. The third row 90 is bent toward the middle row 60 at another perforated latitudinal weld 40 disposed adjacent to the fracture 114. Since the purpose of paramedics applying splints is not to correct alignment of bones but to merely immobilize the wounded area for the purpose of transport of the patient, the splint 10 enables paramedics to do so without restricting crucial blood flow to the injured area and without necessarily preventing temporary access to the wound for interim treatment.

The length of the splint 10 may range from a small size, such as 12 inches or less for a wrist or a child's arm, to a large size, such as 30 inches or more for a lower body part related to the leg or foot. The width may vary from a small size, such as 7 inches or less, to a large size, such as 18 inches or more.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention which could be more broadly or narrowly defined later by patent claims.

The words used in this specification to describe the invention, and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in later in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in later defined claims or that a single element may be substituted for two or more elements in later defined claims.

Insubstantial changes from the claimed subject matter as viewed by a person with ordinary skill in the art, now known or later devised, are expressly contemplated as being equivalently within the scope of the invention. Therefore, obvious substitutions now or later known to one with ordinary skill in the art are defined to be within the scope of the defined elements.

The invention is thus to be understood to include what is specifically illustrated and described above, what is conceptionally equivalent, what can be obviously substituted and also what essentially incorporates the essential idea of the invention.

What is claimed is:

1. An inflatable splint comprising:
   a first portion including a first plurality of air chambers;
   a second portion including a second plurality of air chambers;
   a plurality of longitudinal divisions separating the first portion into a plurality of air chambers and the second portion into a plurality of air chambers;
   a separable latitudinal dividing portion dividing a first portion of the plurality of longitudinal air chambers from a second portion of the longitudinal air chambers; the separable latitudinal dividing portion comprising a means for selectively separating the first portion from the second portion along a part of the separable latitudinal dividing portion; and
   a fastener to couple a first edge of the first portion to a second edge of the first portion.

2. The splint of claim 1 wherein the separable latitudinal dividing portion comprises a latitudinal weld with a perforation defined in the weld.

3. The splint of claim 1 wherein the perforated latitudinal dividing portion enables part of the first portion to be severed from and to be folded away from the second portion.

4. The splint of claim 2 wherein the second portion is detachable at least in part from the first portion by way of the perforated latitudinal dividing portion.

5. The splint of claim 1 wherein the first portion is adapted to wrap around a first portion of an extremity of a human body.

6. The splint of claim 5 the first portion is capable of forming a first U-structure.

7. The splint of claim 5 wherein the second portion is adapted to wrap around a second portion of the extremity of the human body.

8. The splint of claim 7 wherein the second portion is capable of forming a second U-structure.

9. The splint of claim 1 wherein:
   the first portion is capable of forming a first U-structure;
   the second portion is capable of forming a second U-structure; and
   the second U-structure is capable of being disposed at least in part within the first U-structure.

10. The splint of claim 1 further comprising a blow spout coupled to at least one air chamber and wherein the air chambers are intercommunicated with each other and form a common inflatable containment.

11. The splint of claim 1 wherein the first portion further comprises the fastener to couple a first edge of the first portion to a second edge of the first portion.

12. The splint of claim 11 wherein the fastener is a first fastener and further comprising a second fastener to couple a right edge of the second portion to a left edge of the second portion.

13. The splint of claim 12 wherein the first fastener and the second fastener each comprise a hook and loop strap.

14. The splint of claim 1 wherein the first portion further comprises an attachment mechanism to couple the first portion to the second portion when the first and second portions are disposed adjacent to each other and are overlapped to a selectively varied degree.

15. The splint of claim 14 wherein the attachment mechanism comprises double sticky tape adhered to the first portion and capable when a release strip is removed to adhere to the second portion when the first and second portions are disposed adjacent to each other.

16. An inflatable splint comprising:
   a plurality of longitudinal air chambers disposed side by side;
   a plurality of longitudinal welds separating the air chambers disposed side by side;
   a separable latitudinal dividing portion dividing a first portion of the plurality of longitudinal air chambers from a second portion of the plurality of longitudinal air chambers; and
   wherein the separable latitudinal dividing portion comprises a latitudinal weld with a perforation defined in the latitudinal weld and extending a substantial portion of the length of the weld for defining a severing line between the first portion and the second portion.

17. The splint of claim 16 wherein the second portion further comprises a second fastener to couple a right edge of the second portion to a left edge of the second portion.

18. The splint of claim 17 wherein the first fastener and the second fastener each comprise a hook and loop strap.

19. The splint of claim 16 wherein a center portion between longitudinal welds and latitudinal welds is uninterupted by welds between opposite ends of at least one of the plurality of longitudinal air chambers, wherein said opposite ends pertain to the first and second portions respectively.

20. A method for securing an extremity of a human body with an inflatable splint, the, inflatable splint having a first portion and a second portion with the first portion and the second portion segmented with longitudinal welds to provide longitudinal air chambers, and the first portion separated from the second portion by a separable latitudinal dividing portion; the method comprising:
   separating the first portion from the second portion,
   inflating the splint,
   surrounding a portion of the extremity with the first portion,
   attaching a first edge of the first portion to a second edge of the first portion,
   selectively bending the second portion generally about a line parallel to the separable latitudinal dividing portion, and
   selecting overlapping and attaching the second portion on the first portion to selectively fix an angle of bend between the first portion and the second portion.

21. The method in claim 20 further comprising perforating the latitudinal weld.

22. The method in claim 21 further comprising detaching at least in part the first portion from the second portion.

23. The method in claim 20 wherein the separable latitudinal dividing portion comprises a latitudinal weld with a perforation therein and wherein said separating the first portion from the second portion comprises detaching at least in part the first portion from the second portion by tearing along the perforated latitudinal weld.

24. The method in claim 20 wherein said surrounding a portion of the extremity comprises wrapping the first portion of the inflatable splint around the extremity by forming a first U-structure with the first portion.

25. The method in claim 24 further comprising fastening a left side of the first portion to a right side of the first portion.

26. The method in claim 20 further comprising wrapping the second portion of the inflatable splint around another potion of the extremity.

27. The method in claim 26 wherein said wrapping the second portion around another portion of the extremity comprises forming a second U-structure with the second portion.

28. The method in claim 20 further comprising fastening a left side of the second portion to a right side of the second portion.

* * * * *